(12) United States Patent
Ito et al.

(10) Patent No.: US 11,193,941 B2
(45) Date of Patent: Dec. 7, 2021

(54) METHOD FOR EVALUATING CONDITION OF SKIN DRYNESS

(71) Applicant: KAO CORPORATION, Tokyo (JP)

(72) Inventors: Shotaro Ito, Utsunomiya (JP); Junko Ishikawa, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 440 days.

(21) Appl. No.: 15/308,724

(22) PCT Filed: May 8, 2015

(86) PCT No.: PCT/JP2015/063962
§ 371 (c)(1),
(2) Date: Nov. 3, 2016

(87) PCT Pub. No.: WO2015/170781
PCT Pub. Date: Nov. 12, 2015

(65) Prior Publication Data
US 2017/0192015 A1    Jul. 6, 2017

(30) Foreign Application Priority Data

May 8, 2014 (JP) .............................. JP2014-096727
Mar. 17, 2015 (JP) .............................. JP2015-053289

(51) Int. Cl.
*G01N 33/68* (2006.01)
*C12Q 1/533* (2006.01)
*G01N 33/50* (2006.01)

(52) U.S. Cl.
CPC ......... *G01N 33/6893* (2013.01); *C12Q 1/533* (2013.01); *G01N 33/6881* (2013.01); *G01N 33/50* (2013.01); *G01N 2333/99* (2013.01); *G01N 2500/00* (2013.01); *G01N 2800/20* (2013.01)

(58) Field of Classification Search
CPC ........... G01N 33/6893; G01N 33/6881; G01N 2800/20; G01N 2500/00; G01N 2333/99; G01N 33/50; C12Q 1/533
See application file for complete search history.

(56) References Cited

U.S. PATENT DOCUMENTS

| | | | |
|---|---|---|---|
| 2004/0146907 A1* | 7/2004 | Smith .................. | C12Q 1/6886 435/6.14 |
| 2010/0076071 A1* | 3/2010 | Lephart ................. | A61K 8/498 514/456 |
| 2012/0302572 A1* | 11/2012 | Kan ...................... | C12Q 1/6886 514/249 |
| 2012/0302649 A1 | 11/2012 | Hibino et al. | |
| 2013/0225662 A1* | 8/2013 | Kennedy ............. | C12Q 1/6886 514/44 R |
| 2015/0118686 A1 | 4/2015 | Hibino et al. | |

FOREIGN PATENT DOCUMENTS

| | | |
|---|---|---|
| CN | 101039650 A | 9/2007 |
| CN | 101971025 A | 2/2011 |
| CN | 102625853 A | 8/2012 |
| EP | 2 508 605 A1 | 10/2012 |
| JP | 2006-526383 A | 11/2006 |
| KR | 10-2012-0058863 A | 6/2012 |
| WO | WO 2004/056858 A2 | 7/2004 |
| WO | WO 2011/068166 A | 6/2011 |
| WO | WO 2012/074202 A2 | 6/2012 |
| WO | WO2012151346 * | 11/2012 ............ A61K 33/00 |

OTHER PUBLICATIONS

Park et al. (PNAS, Apr. 28, 2009, vol. 106, No. 17, pp. 6950-6955).*
Miriam Webster Dictionary (retrieved from https://www.merriam-webster.com/medical/actinic%20keratosis on May 24, 2019).*
Fabbrocini et qal. (Journal of Experimental & Clinical Cancer Research 2012;vol. 31, Article No. 50).*
Di Franco et al,2013; Radiation Oncology vol. 8, Article No. 57).*
Ishikawa et al (J. of cosmetic Dermatology,2012; 12, 3011).*
International Search Report and Written Opinion of the International Searching Authority dated Jul. 22, 2015, in PCT/JP2015/063962 filed May 8, 2015.
Warner, R.R. et al., "Correlation of Water Content with Ultrastructure in the Stratum Corneum", CRC Press, Inc., (1994), pp. 3-12.
Simon, M. et al., "Persistence of Both Peripheral and Non-Peripheral Corneodesmosomes in the Upper Stratum Corneum of Winter Xerosis Skin Versus only Peripheral in Normal Skin", The Society for Investigative Dermatology, Inc., vol. 116, No. 1, (2001), pp. 23-30.
Harding, C.R. et al., "The cornified cell envelope: an important marker of stratum corneum maturation in healthy and dry skin", International Journal of Cosmetic Science. vol. 25, No. 4, (2003), pp. 157-167.
Delattre, C. et al., "Proteomic analysis identifies new biomarkers for postmenopausal and dry skin", Experimental Dermatology, vol. 21, No. 3, (2012), pp. 205-210.
Persson, S. et al.. "Diversity of the protein disulfide isomerase family: Identification of breast tumor induced Hag2 and Hag3 as novel members of the protein family", Science Direct: Molecular Phylogenetics and Evolution, vol. 36, No. 3, (2005), pp. 734-740.
Gray, T. A. et al.. "Anterior Gradient-3: A novel biomarker for ovarian cancer that mediates cisplatin resistance in xenograft models", Journal of Immunological Methods, vol. 378, Nos. 1-2, (2012), pp. 20-32.
Park, S-W et al., "The protein disulfide isomerase AGR2 is essential for production of intestinal mucus", Proceedings of the National Academy of Science, vol. 106, No. 17, (2009), pp. 6950-6955.
Zhao, F. et al., "Disruption of Paneth and goblet cell homeostasis and increased endoplasmic reticulum stress in Agr2-/- mice", Developmental Biology, vol. 338, No. 2, (2010), pp. 270-279.
Elizabeth A. Wayner, et al., "Development of an ELISA to detect the secreted prostate cancer biomarker AGR2 in voided urine", The Prostate, vol. 72, No. 9, 2012, pp. 1023-1034.

* cited by examiner

*Primary Examiner* — Carmencita M Belei
(74) *Attorney, Agent, or Firm* — Oblon, McClelland, Maier & Neustadt, L.L.P.

(57) ABSTRACT

To provide a method for quickly and accurately evaluating a condition of skin dryness and a method for efficiently searching a substance to improve dry skin. A method for evaluating a condition of skin dryness, the method comprising measuring the expression levels of AGR2 and/or AGR3 in skin cells collected from subjects.

8 Claims, 2 Drawing Sheets

[Fig. 1]
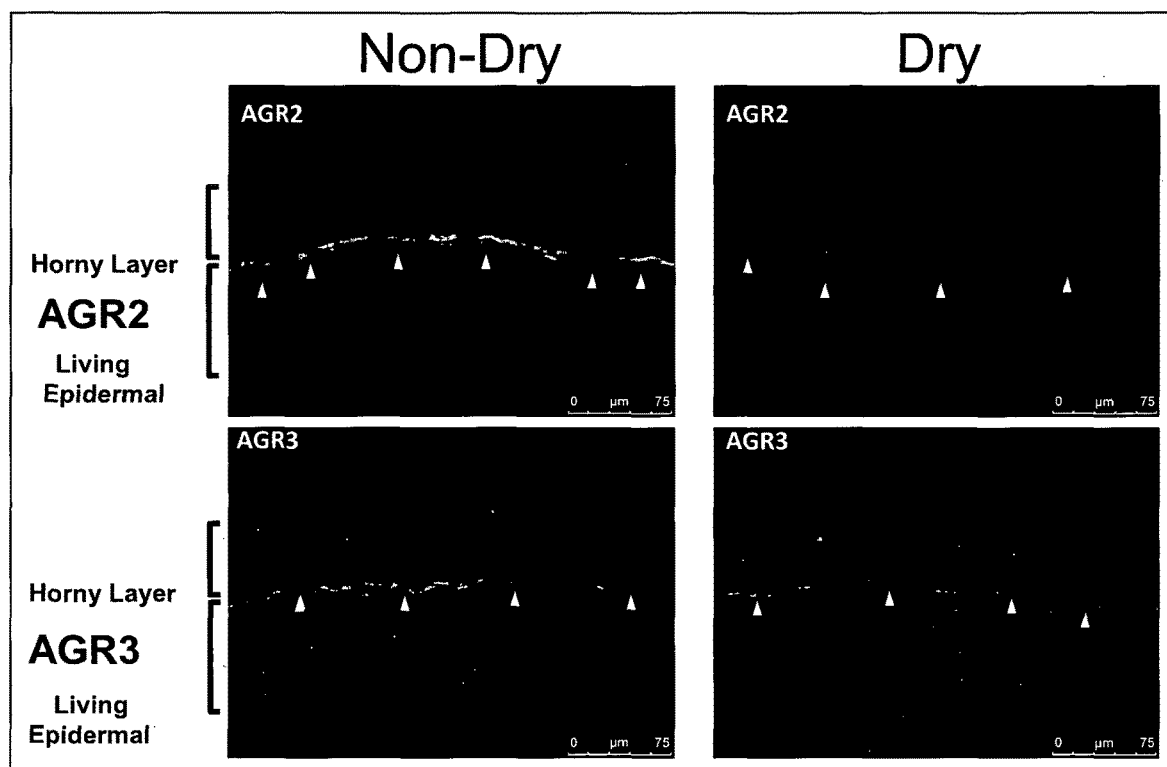

[Fig. 2]
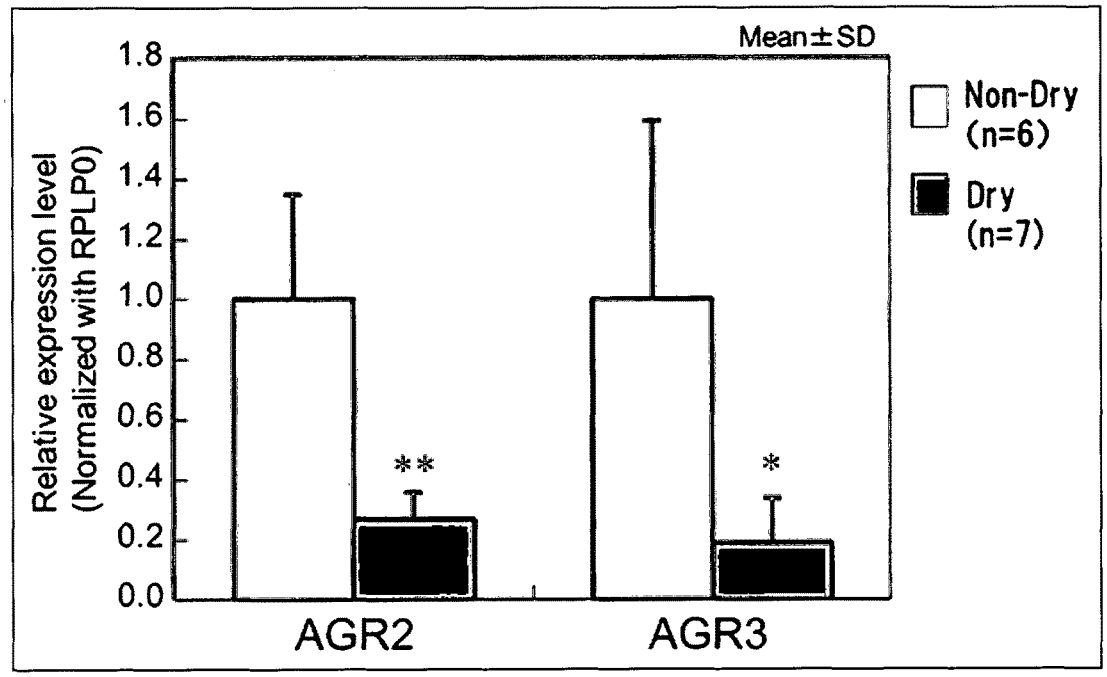
[Fig. 3]
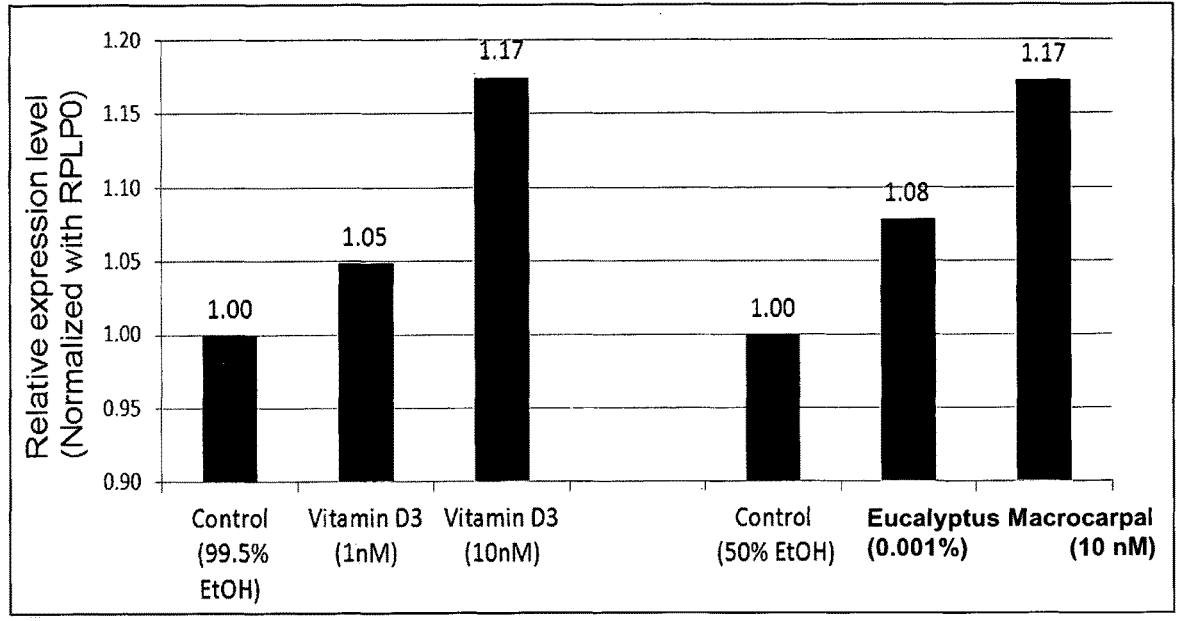

METHOD FOR EVALUATING CONDITION OF SKIN DRYNESS

FIELD OF THE INVENTION

The present invention relates to a method for evaluating a condition of skin dryness and a method for searching a substance to ameliorate dry skin.

BACKGROUND OF THE INVENTION

The normal skin is provided with the function of retaining moisture (moisture retention function). The softness of skin is retained by this moisture retention function and a good condition can be also retained by maintaining a barrier function. Meanwhile, when the moisture retention function of skin declines and skin is then dried, the skin condition worsens, and rough skin occurs.

It has been reported that a decline in the water content of the horny layer (Non Patent Literature 1), the survival of corneocyte adhesion structure (corneodesmosome) in the upper horny layer (Non Patent Literature 2) and an increase in corneocytes with immature marginal zones (cornified envelope) (Non Patent Document 3) are observed in dry skin. In recent years, it has been also reported that corneodesmosin, annexin A2 and phosphatidylethanolamine-binding protein 1 increase in dry skin by global proteomic analysis (two dimensional electrophoresis) of the horny layer collected by tape stripping (Non Patent Literature 4). However, prior reports on dry skin have focused attention on the structure and components of dead cells (horny layer), and living skin cells (living subcorneal cells) have not been analyzed.

Both AGR2 (Anterior gradient homolog 2) and AGR3 (Anterior gradient homolog 3) are proteins belonging to the Protein disulfide isomerase (PDI) family. Both AGR2 and AGR3 have one thioredoxin domain (CXXS), and are believed to be bound to a protein S—S bond site and involved in protein folding and maturation (Non Patent Literatures 5 and 6). In fact, it has been reported that AGR2 is bound to mucin in the intestines to be involved in mucin maturation and is expressed in breast cancer cells, and AGR3 is expressed in ovarian cancer cells (Non Patent Literatures 7-9). However, the functions of AGR2 and AGR3 in skin have not been reported until now.

CITATION LIST

Non Patent Literature

Non Patent Literature 1: Bioengineering of the skin: Water and the stratum corneum. Elsner P, Berardesca E and Maibach H I (eds.), CRC Press Inc, 3-12, 1994
Non Patent Literature 2: J Invest Dermatol, 116(1):23-30, 2001
Non Patent Literature 3: Int J Cosmet Sci, 25(4):157-167, 2003
Non Patent Literature 4: Exp Dermatol, 21(3):205-210, 2012
Non Patent Literature 5: Mol Phylogenet Evol, 36(3):734-740, 2005
Non Patent Literature 6: J Immunol Methods, 378(1-2):20-32, 2012
Non Patent Literature 7: Proc Natl Acad Sci, 106(17):6950-6955, 2009
Non Patent Literature 8: Dev Biol, 338(2):270-279, 2010
Non Patent Literature 9: J Immunol Methods, 378(1-2):20-32, 2012

SUMMARY OF THE INVENTION

The present invention provides a method for evaluating a condition of skin dryness, the method comprising measuring the expression levels of AGR2 and/or AGR3 in skin cells collected from a subject.

The present invention further provides a method for evaluating or selecting an agent for ameliorating dry skin, the method comprising the following (A) to (D):

(A) administering a test substance to a subject or a subject animal;

(B) measuring the expression levels of AGR2 and/or AGR3 in skin cells collected from the subject or subject animal;

(C) comparing the expression levels measured in the (B) with the expression levels of AGR2 and/or AGR3 in skin cells collected from a subjects or a subject animal to which the test substance is not administered; and (D) evaluating the effect of the test substance to increase the expression levels of AGR2 and/or AGR3 based on the result of the (C).

The present invention further provides a method for evaluating or selecting an agent for ameliorating dry skin, the method comprising the following (A') to (D'):

(A') contacting a test substance with a tissue or cells which are derived from a mammal and which can express AGR2 and/or AGR3 can be expressed;

(B') measuring the expression levels of AGR2 and/or AGR3 in the tissue or cells;

(C') comparing the expression levels measured in the (B') with the expression levels of AGR2 and/or AGR3 in a control group; and (D') evaluating the effect of the test substance to increase the expression levels of AGR2 and/or AGR3 based on the result of the (C').

BRIEF DESCRIPTION OF THE DRAWINGS

FIG. 1 is the expression patterns of AGR2 and AGR3 in skin tissue. Non-Dry: healthy people, Dry: people with dry skin.

FIG. 2 is the expression levels of AGR2 and AGR3 mRNA in skin tissue. Non-Dry: healthy people, Dry: people with dry skin, *: $p<0.05$, **: $p<0.01$ (T-test).

FIG. 3 is the influence of humectants on AGR2 expression. $n=2$ in each data.

DETAILED DESCRIPTION OF THE INVENTION

In the present description, "a condition of skin dryness" can be also referred to as a condition of skin moisture retention. As the degree of skin dryness is stronger, skin retains less moisture, and a subject has a higher degree of dry skin. Conversely, as the degree of skin dryness is weaker, skin retains more moisture, and a subject has a milder degree of dry skin or does not have dry skin.

In the present description, "rough skin caused by skin dryness" (in the present description, can be simply referred to as "rough skin") means a worsened condition of skin which is caused by losing the softness and barrier function of skin due to a decline in the moisture retention function of skin. Examples of rough skin caused by dryness include, for example, dry skin, sensitive skin, xeroderma, senile xerosis, ichthyosis and dry eczema.

In the present description, "skin cells collected from a subject (or subject animal)" include living cells in skin tissue in which AGR2 and/or AGR3 can be expressed, preferably living epidermal cells. The living epidermal cells are a cell group found in deeper layer than the horny layer in epidermal tissue. The living epidermal cells from a subject (or subject animal) can be collected by, after collecting skin tissue by a common means such as punch biopsy, separating the epidermis and dermis by e.g. dispase treatment.

In the present description, the "expression of AGR2 and/or AGR3" means the expression of at least one of the AGR2 gene and AGR3 gene or both, or the expression of at least one of the AGR2 protein and AGR3 protein or both. When detected at an mRNA level, the expression level of the AGR2 gene or AGR3 gene can be measured by, for example, a Real-Time RT-PCR method or RNase protection assay after extracting total RNA from cells, or detecting and quantitatively determining mRNA into which the AGR2 gene or AGR3 gene is transcribed using e.g. Northern blot analysis. The expression level of the AGR2 protein or AGR3 protein can be measured by common immunoassay such as an RIA method, an EIA method, ELISA, a bioassay, proteome and Western blot. Among these, Western blot is inexpensive and simple.

The present invention relates to providing a method for quickly and accurately evaluating a condition of skin dryness or a condition of rough skin caused by skin dryness, and providing a method for efficiently searching a substance to ameliorate rough skin caused by skin dryness.

The present inventors focused attention on living skin cells (living subcorneal cells), which have not been researched in relation to the water content of skin until now, and intensively made investigations to search an index to relate the activity of these cells with the water content of skin. As a result, the present inventors found that the expression of AGR2 and AGR3, which has not been conventionally reported to have a function on skin, was a good index to indicate a condition of skin dryness.

According to the present invention, a condition of skin dryness or a condition of rough skin caused by skin dryness in a subject can be quickly and accurately evaluated. According to the present invention, a substance to ameliorate a condition of dry skin or a condition of rough skin caused by skin dryness can be also efficiently searched.

As shown in examples described below, the expression levels of AGR2 and AGR3 in skin cells both decrease in subjects with dry skin compared to those in subjects without dry skin. In addition, the expression levels of AGR2 and AGR3 are correlated with the skin dryness score and horny layer conductance, which are known as indexes of a condition of skin dryness. Therefore, the expression levels of AGR2 and/or AGR3 can be an index to reflect a condition of skin dryness in subjects.

One embodiment of the present invention is therefore a method for evaluating a condition of skin dryness, the method comprising measuring the expression levels of AGR2 and/or AGR3 in skin cells collected from a subject. In an embodiment of such method, an evaluation for a condition of skin dryness is an evaluation for a condition of rough skin caused by skin dryness. The subjects to which such method is applied include subjects who desire to prevent or ameliorate dry skin or sensitive skin, or desire to know a risk for dry skin or sensitive skin for non-therapeutic purposes such as cosmetic purposes, and subjects who desire to prevent or ameliorate skin symptoms or conditions caused by dryness, such as xeroderma, senile xerosis, ichthyosis and dry eczema. The measuring procedure for the expression levels of AGR2 and/or AGR3 in such method is as described above.

In the above method, a condition of skin dryness or a condition of rough skin of a subject is evaluated based on the measured expression levels of AGR2 and/or AGR3. It is preferred that the expression levels of both AGR2 and AGR3 be used as an index.

In an embodiment of the above evaluation, when the expression levels of AGR2 and/or AGR3 in skin cells of a subject are low, the skin of the subject is evaluated as being in a dry condition or rough skin. On the other hand, when the expression levels of AGR2 and/or AGR3 are high, the skin of the subject is evaluated as not being in a dry condition or rough skin. The degree of expression level can be determined by comparison with reference values which are defined in advance. As the reference value, an index of the expression levels of AGR2 and/or AGR3 acquired from the group of dry skin or rough skin (hereinafter, reference value 1), or an index of the expression levels of AGR2 and/or AGR3 acquired from the group of non-dry skin or non-rough skin (hereinafter, reference value 2) can be used. Specific examples of the reference value 1 include the mean value of the expression levels of AGR2 and/or AGR3 in skin cells (e.g. living epidermal cells) collected from the group of dry skin or rough skin. Specific examples of the reference value 2 include the mean value of the expression levels of AGR2 and/or AGR3 in skin cells (e.g. living epidermal cells) collected from the group of non-dry skin or non-rough skin. Examples of the group of non-dry skin or non-rough skin include a human group with a skin dryness score of 1.5 or less, preferably a human group with a skin dryness score of 1 or less. Examples of the group of dry skin or rough skin include a human group with a skin dryness score of more than 2.5, preferably a human group with a skin dryness score of more than 3. In the present description, the "dryness score" of skin is a value obtained by visually evaluating the dry condition of a target site using 5 levels (0: no dryness, 1: slight flaking is observed, 2: moderate flaking and/or scaling are observed, 3: marked scaling and/or slight fissuring are observed, and 4: severe scaling and/or fissuring are observed). In the present embodiment, however, the reference values are not limited to the above values and appropriate values which can reflect an actual condition of skin dryness can be properly defined.

For example, when the measured values of the expression levels of AGR2 and/or AGR3 from a subject are equal to or lower than the reference value 1, the skin of such subject is evaluated as being in a dry condition or rough skin. For example, when the measured values of the expression levels of AGR2 and/or AGR3 from a subject are equal to or higher than the reference value 2, the skin of such subject is evaluated as not being in a dry condition or rough skin. For example, when the measured values of the expression levels of AGR2 and/or AGR3 from a subject are higher than the reference value 1 and lower than the reference value 2, the skin of such subject is evaluated as being in a slightly dry condition or in a high risk condition for dry skin and rough skin.

For example, when the measured values of the expression levels of AGR2 and/or AGR3 from a subject are 50% or less of the reference value 2, preferably 30% or less and more preferably 25% or less, the skin of such subject is evaluated as being in a dry condition or rough skin.

Alternatively, when the expression levels of AGR2 and/or AGR3 in skin cells are equal to or lower than the reference value 1, the skin cells are evaluated as being skin cells derived from a subject whose skin is in a dry condition or rough skin. On the other hand, when the expression levels of AGR2 and/or AGR3 in skin cells are equal to or higher than the reference value 2, the skin cells are evaluated as being skin cells derived from a subject whose skin is not in a dry condition or rough skin. Alternatively, when the measured values of the expression levels of AGR2 and/or AGR3 in skin cells are higher than the reference value 1 and lower than the reference value 2, the skin cells are evaluated as being skin cells derived from a subject whose skin is in a slightly dry condition or who has a high risk for dry skin and rough skin.

Alternatively, when the measured values of the expression levels of AGR2 and/or AGR3 in skin cells are 50% or less of the reference value 2, preferably 30% or less and more preferably 25% or less, the skin cells are evaluated as being skin cells derived from a subject whose skin is in a dry condition or rough skin.

In another embodiment of the above evaluation, the expression levels of AGR2 and/or AGR3 in skin cells of a subject are measured over time. The frequency of measurement over time includes, but not limited to, for example, every week, every two weeks and every month. The number of times of measurement only has to be twice or more, preferably three times or more. For example, when the expression levels of AGR2 and/or AGR3 decrease compared to those of the last measurement, the skin of a subject is evaluated as having dryness which becomes worse or rough skin which becomes worse. On the other hand, when the expression levels of AGR2 and/or AGR3 increase compared to those of the last measurement, the skin of a subject is evaluated as having dryness which has ameliorated or rough skin which has ameliorated. For example, when the expression levels of AGR2 and/or AGR3 are measured three times or more over time and continuously decrease from the first measurement, the skin of a subject is evaluated as having dryness which becomes worse or rough skin which becomes worse. On the other hand, when the expression levels of AGR2 and/or AGR3 continuously increase from the first measurement, the skin of a subject is evaluated as having dryness which has ameliorated or rough skin which has ameliorated.

Alternatively, when the expression levels of AGR2 and/or AGR3 in skin cells decrease compared to those of the last measurement, the skin cells are evaluated as being skin cells derived from a subject in whom skin dryness becomes worse or rough skin becomes worse. On the other hand, when the expression levels of AGR2 and/or AGR3 in skin cells increase compared to those of the last measurement, the skin cells are evaluated as being skin cells derived from a subject in whom skin dryness has ameliorated or rough skin has ameliorated. Alternatively, when the expression levels of AGR2 and/or AGR3 in skin cells continuously decrease from those of the first measurement, the skin cells are evaluated as being skin cells derived from a subject in whom skin dryness becomes worse or rough skin becomes worse. On the other hand, when the expression levels of AGR2 and/or AGR3 in skin cells continuously increase from those of the first measurement, the skin cells are evaluated as being skin cells derived from a subject in whom skin dryness has ameliorated or rough skin has ameliorated.

In yet another embodiment of the above evaluation, a comparison with the above reference values and a comparison over time can be combined. In the present embodiment, the expression levels of AGR2 and/or AGR3 in skin cells of a subject are measured over time. The frequency of measurement over time and the number of times are the same as above. Each measured value in each time is compared with the reference values by the above-described procedure, and further the measured values of the second measurement and subsequent measurement are also compared with the earlier measured values by the above-described procedure. In the present embodiment, a condition of skin dryness and a condition of rough skin of a subject can be evaluated in more detail by comprehensively investigating the comparative results with the reference values and comparative results with the earlier measured values.

As described above, a decline in the expression levels of AGR2 and/or AGR3 is related to skin dryness. Therefore, a substance to increase the expression levels of AGR2 and/or AGR3 can raise the moisture retention function of skin and ameliorate dry skin or rough skin.

Another embodiment of the present invention is therefore a method for evaluating or selecting an agent for ameliorating dry skin or an agent for ameliorating rough skin, the method comprising the following (A) to (D):

(A) administering a test substance to a subject or a subject animal;

(B) measuring the expression levels of AGR2 and/or AGR3 in skin cells collected from the subject or subject animal;

(C) comparing the expression levels measured in the (B) with the expression levels of AGR2 and/or AGR3 in skin cells collected from a subjects or a subject animal to which the test substance is not administered; and (D) evaluating the effect of the test substance to increase the expression levels of AGR2 and/or AGR3 based on the result of the (C).

The subject animals can include non-human animals, for example, mice, rats, hamsters, marmots, rabbits, cats, dogs, pigs and primates such as monkeys, and rodents such as rats and mice are preferred in terms of easy acquisition and handling.

The test substance administered to the subject or subject animal is not particularly restricted as long as it is desired to be used as an agent for ameliorating dry skin or an agent for ameliorating rough skin. The test substance can be a naturally occurring substance or a substance artificially synthesized by e.g. a chemical or biological method, and can be a compound, or a composition or a mixture. The method for administering the test substance is not particularly limited, and, for example, dermal administration, oral administration, radiation and inhalation are preferred in terms of simplicity and low invasiveness. The administration period can be set in a range of a day to several months and the frequency of administration can be also set in a range of once to several times a day.

Next, the expression levels of AGR2 and/or AGR3 in skin cells collected from the subject or subject animal (test group) are measured. The measuring procedure for expression levels is as described above.

Further, the expression levels of AGR2 and/or AGR3 in skin cells collected from a subject or a subject animal to which the above test substance is not administered (control group) are measured. The control groups include, for example, skin cells collected from the same subject or subject animal before the test substance is administered, skin cells collected from a skin region to which the test substance is not administered or a skin region to which a control substance is administered in the same subject or subject animal, skin cells collected from a subject or subject animal to which the test substance is not administered. The measuring procedure for expression levels is as described above.

Next, the expression levels of AGR2 and/or AGR3 are compared between the test group and control group. Preferably, the expression levels of both AGR2 and AGR3 are compared. When the expression levels of AGR2 and/or AGR3 in the test group increase compared to those in the control group, the above test substance is evaluated as having an effect of increasing the expression levels of AGR2 and/or AGR3. This test substance evaluated as having an effect of increasing the expression levels of AGR2 and/or AGR3 is selected as an agent for ameliorating dry skin or rough skin.

For example, when the expression levels of AGR2 and/or AGR3 in the test group statistically significantly increase compared to the expression levels in the control group, the test substance is evaluated as having an effect of increasing the expression levels of AGR2 and/or AGR3. For example, when the expression levels of AGR2 and/or AGR3 in the control group are considered as 100% and the expression levels in the test group are 105% or more, preferably 110% or more and more preferably 120% or more, the test substance is evaluated as having an effect of increasing the expression levels of AGR2 and/or AGR3. This test substance having an effect of increasing the expression levels of AGR2 and/or AGR3 is selected as an agent for ameliorating dry skin or rough skin.

In addition to the method carried out in vivo as described above, the method for evaluating or selecting an agent for ameliorating dry skin or an agent for ameliorating rough skin by the present invention can be also carried out in vitro or ex vivo. That is, yet another mode of the present invention is a method for evaluating or selecting an agent for ameliorating dry skin or an agent for ameliorating rough skin, the method comprising the following (A') to (D'):

(A') contacting a test substance with a tissue or cells which are derived from a mammal and which can express AGR2 and/or AGR3;

(B') measuring the expression levels of AGR2 and/or AGR3 in the tissue or cells;

(C') comparing the expression levels measured in the (B') with the expression levels of AGR2 and/or AGR3 in a control group; and (D') evaluating the effect of the test substance to increase the expression levels of AGR2 and/or AGR3 based on the result of the (C').

In the above method, the type of test substance which can be used is the same as of the above-described in vivo method.

Examples of the tissue or cells which are derived from a mammal and which can express AGR2 and/or AGR3, which are used in the above (A'), include tissues or cells which have been isolated from a mammal and which can express the AGR2 gene or AGR3 gene or the AGR2 protein or AGR3 protein, or a cultured substance thereof. Such isolated tissue or cells, or cultured substance thereof include an isolated skin tissue or isolated skin cells, preferably living epidermal cells, and a cultured substance thereof; for example, an enterocyte line, a breast cancer cell line and an ovarian cancer cell line.

Alternatively, examples of the tissue or cells which are derived from a mammal and which can express AGR2 and/or AGR3, used in the above (A'), include tissues or cells of mammals which are genetically modified so that the AGR2 gene or AGR3 gene or the AGR2 protein or AGR3 protein will be expressed, or cultured substances thereof. Such tissues or cells of mammals which are genetically modified, and cultured substances thereof can be created, for example, by introducing the genes coding for AGR2 protein and/or AGR3 protein into any tissues or cells in mammals and transforming the tissues or cells so that AGR2 and/or AGR3 will be expressed or the expression of AGR2 and/or AGR3 will be reinforced. The methods for introducing a gene into cells include, but not limited to, vector introduction by e.g. electroporation and lipofection.

Examples of mammals from which the tissues or cells which can express AGR2 and/or AGR3 are derived, used in the method of the present invention, include, but not limited to, human, mice, rats, hamsters, marmots, rabbits, cats, dogs, pigs and monkeys.

The tissue or cells which can express AGR2 and/or AGR3 can be brought into contact with a test substance by, for example, after adding a test substance to a culture fluid in advance so that a fixed concentration will be obtained, putting such tissue or cells on the culture fluid, or adding a test substance to a culture fluid on which such tissue or cells are put so that a fixed concentration will be obtained. It is preferred that the tissue or cells after the contact be cultured, for example, at room temperature (25° C.) to 37° C. commonly for 3 to 48 hours. Commonly used media can be used as media to culture the above tissue or cells.

In the above (B'), the expression levels of AGR2 and/or AGR3 in the tissue or cells brought into contact with a test substance (test group) are measured. The measuring procedure for the expression levels of AGR2 and/or AGR3 is as described above.

The control group in the above (C') includes the same tissue or cells derived from a mammal which can express AGR2 and/or AGR3 as in the test group, wherein the tissue or cells are not brought into contact with a test substance. Alternatively, the control groups include, for example, tissues or cells derived from mammals which do not naturally have or hardly have the expression ability of AGR2 and/or AGR3; and the same tissue or cells as in the test group which have been modified so that AGR2 and/or AGR3 will not be expressed or the tissue or cells described above which are further brought into contact with a test substance. The tissue or cells which have been modified so that AGR2 and/or AGR3 will not be expressed include, for example, knockdown cells by siRNA, and a tissue or cells derived from AGR2 and/or AGR3 knockout mice. The measuring procedure for the expression levels of AGR2 and/or AGR3 in the control group is as described above.

Next, the expression levels of AGR2 and/or AGR3 are compared between the test group and control group. Preferably, the expression levels of both AGR2 and AGR3 are compared. When the expression levels of AGR2 and/or AGR3 in the test group increase compared to those in the control group, the above test substance is evaluated as having an effect of increasing the expression levels of AGR2 and/or AGR3, and selected as an agent for ameliorating dry skin or rough skin. The comparison between the test group and the control group, and the evaluation of a test substance and the selection procedure are the same as in the above-described in vivo method.

The selected substances can be further screened in any of the above in vivo method and in vitro method or ex vivo method as needed. For example, a test substance evaluated or selected as an agent for ameliorating dry skin or rough skin by the above method is administered to, for example, a subject, a subject animal and cultured skin derived therefrom to directly examine the influence on the moisture retention ability of skin. Hereby, a substance having a stronger action to ameliorate dry skin or rough skin can be further selected. The moisture retention ability of skin can be measured based on, for example, transepidermal water loss (TEWL), skin dryness score, horny layer conductance, and the amount of moisture retention components in the horny layer (NMF, ceramide etc.).

The following compositions, production methods, uses or methods are further disclosed in the present description as the illustrative embodiments of the present invention. It is noted, however, that the present invention is not restricted to these embodiments.

<1> A method for evaluating a condition of skin dryness, the method comprising measuring the expression levels of AGR2 and/or AGR3 in skin cells collected from a subject.

<2> The method according to <1>, wherein the condition of skin dryness is preferably a condition of rough skin caused by skin dryness.

<3> The method according to <2>, wherein the rough skin caused by skin dryness is preferably selected from the group consisting of dry skin, sensitive skin, xeroderma, senile xerosis, ichthyosis and dry eczema.

<4> The method according to any one of <1> to <3>, wherein the subject is preferably a subject who desires to prevent or ameliorate dry skin or sensitive skin for non-therapeutic purposes, a subject who desires to know a risk for dry skin or sensitive skin for non-therapeutic purposes, or a subject who desires to prevent or ameliorate symptoms or conditions selected from the group consisting of xeroderma, senile xerosis, ichthyosis and dry eczema.

<5> The method according to any one of <1> to <4>, preferably further comprising acquiring the mean value of the expression levels of AGR2 and/or AGR3 in skin cells collected from the group of dry skin or rough skin as the reference value 1.

<6> The method according to any one of <1> to <4>, preferably further comprising acquiring the mean value of the expression levels of AGR2 and/or AGR3 in skin cells collected from the group of non-dry skin or non-rough skin as the reference value 2.

<7> The method according to <5>, wherein the group of dry skin or rough skin is preferably a human group with a skin dryness score of more than 2.5 and more preferably a human group with a skin dryness score of more than 3.

<8> The method according to <6>, wherein the group of non-dry skin or non-rough skin is preferably a human group with a skin dryness score of 1.5 or less and more preferably a human group with a skin dryness score of 1 or less.

<9> The method according to any one of <5> to <8>, preferably further comprising comparing the expression levels of AGR2 and/or AGR3 in the skin cells of the subject with the reference value 1 or reference value 2.

<10> The method according to <9>, preferably further comprising, when the expression levels of AGR2 and/or AGR3 in the skin cells of the subject are equal to or lower than the reference value 1, evaluating a skin of the subject as being in a dry condition or rough skin.

<11> The method according to <9>, preferably further comprising, when the expression levels of AGR2 and/or AGR3 in the skin cells of the subject are equal to or higher than the reference value 2, evaluating a skin of the subject as not being in a dry condition or rough skin.

<12> The method according to <9>, preferably further comprising, when the expression levels of AGR2 and/or AGR3 in the skin cells of the subject are 50% or less of the reference value 2, preferably 30% or less and more preferably 25% or less, evaluating a skin of the subject as being in a dry condition or rough skin.

<13> The method according to any one of <1> to <12>, wherein the skin cells are preferably living epidermal cells.

<14> The method according to any one of <1> to <13>, wherein the measurement of the above expression levels of AGR2 and/or AGR3 is preferably:

the quantitative determination of AGR2 and/or AGR3 mRNA by a Real-Time RT-PCR method, RNase protection assay or Northern blot analysis, or the measurement of the expression levels of the AGR2 protein and/or AGR3 protein by an RIA method, an EIA method, ELISA, a bioassay, proteome or Western blot.

<15> A method for evaluating or selecting an agent for ameliorating dry skin, the method comprising the following (A) to (D):

(A) administering a test substance to a subject or a subject animal;

(B) measuring the expression levels of AGR2 and/or AGR3 in skin cells collected from the subject or subject animal;

(C) comparing the expression levels measured in the (B) with the expression levels of AGR2 and/or AGR3 in skin cells collected from a subject or subject animal to which the test substance is not administered; and (D) evaluating the effect of the test substance to increase the expression levels of AGR2 and/or AGR3 based on the result of the (C).

<16> The method according to <15>, wherein the skin cells are preferably living epidermal cells.

<17> The method according to <15> or <16>, preferably further comprising the following:

(E) selecting the test substance that increases the expression levels of AGR2 and/or AGR3 in the (D) as an agent for ameliorating dry skin based on the evaluation in the (D).

<18> The method according to any one of <15> to <17>, wherein the skin cells collected from a subject or subject animal to which the test substance is not administered are preferably selected from the group consisting of the following:

(1) skin cells collected from the same subject or subject animal before the test substance is administered;

(2) skin cells collected from a skin region to which the test substance is not administered or a skin region to which a control substance is administered in the same subject or subject animal; and (3) skin cells collected from a subject or subject animal to which the test substance is not administered.

<19> The method according to any one of <15> to <18>, wherein, when the expression levels measured in the above (B) statistically significantly increase compared to the expression levels in skin cells collected from a subject or a subject animal to which the test substance is not administered, the test substance is preferably evaluated as having an effect of increasing the expression levels of AGR2 and/or AGR3.

<20> The method according to any one of <15> to <18>, wherein, when the expression level in skin cells collected from a subject or a subject animal to which the test substance is not administered is considered as 100% and the expression levels measured in the above (B) are 105% or more, preferably 110% or more and more preferably 120% or more, the test substance is preferably evaluated as having an effect of increasing the expression levels of AGR2 and/or AGR3.

<21> A method for evaluating or selecting an agent for ameliorating dry skin, the method comprising the following (A') to (D'):

(A') contacting a test substance with a tissue or cells which are derived from a mammal and which can express AGR2 and/or AGR3;

(B') measuring the expression levels of AGR2 and/or AGR3 in the tissue or cells;

(C') comparing the expression levels measured in the (B') with the expression levels of AGR2 and/or AGR3 in a control group; and (D') evaluating the effect of the test substance to increase the expression levels of AGR2 and/or AGR3 based on the result of the (C').

<22> The method according to <21>, preferably further comprising the following:

(E') selecting the test substance that increases the expression levels of AGR2 and/or AGR3 in the (D') as an agent for ameliorating dry skin based on the evaluation in the (D').

<23> The method according to <21> or <22>, wherein the tissue or cells which are derived from a mammal and which can express AGR2 and/or AGR3 are preferably selected from the group consisting of the following:

(1) an isolated skin tissue or isolated skin cells, or a cultured substance thereof;

(2) isolated living epidermal cells, or a cultured substance thereof;

(3) an enterocyte line, a breast cancer cell line, or an ovarian cancer cell line; and (4) a tissue or cells of mammal which are genetically modified so that the AGR2 gene or AGR3 gene, or the AGR2 protein or AGR3 protein will be expressed, or a cultured substance thereof.

<24> The method according to any one of <21> to <23>, wherein the control group is preferably selected from the group consisting of the following:

(1) the tissue or cells which are derived from a mammal and which can express AGR2 and/or AGR3, wherein the tissue or cells are not brought into contact with a test substance;

(2) a tissue or cells derived from a mammal which do not naturally have or hardly have the expression ability of AGR2 and/or AGR3;

(3) the tissue or cells which are derived from a mammal and which can express AGR2 and/or AGR3, which have been modified so that AGR2 and/or AGR3 will not be expressed; and (4) the tissue or cells of the (2) or (3) which are brought into contact with a test substance.

<25> The method according to any one of <21> to <24>, wherein, when the expression levels measured in the above (B') statistically significantly increase compared to the expression levels in the above control group, the test substance is preferably evaluated as having an effect of increasing the expression levels of AGR2 and/or AGR3.

<26> The method according to any one of <21> to <24>, wherein, when the expression levels in the above control group are considered as 100% and the expression levels measured in the above (B') are 105% or more, preferably 110% or more and more preferably 120% or more, the test substance is preferably evaluated as having an effect of increasing the expression levels of AGR2 and/or AGR3.

<27> The method according to any one of <15> to <26>, wherein the measurement of the above expression levels of AGR2 and/or AGR3 is preferably:

the quantitative determination of AGR2 and/or AGR3 mRNA by a Real-Time RT-PCR method, RNase protection assay or Northern blot analysis, or the measurement of the expression levels of the AGR2 protein and/or AGR3 protein by an RIA method, an EIA method, ELISA, a bioassay, proteome or Western blot.

<28> The method according to any one of <15> to <27>, wherein the agent for ameliorating dry skin is an agent for ameliorating rough skin caused by skin dryness.

<29> The method according to <28>, wherein the rough skin caused by skin dryness is selected from the group consisting of dry skin, sensitive skin, xeroderma, senile xerosis, ichthyosis and dry eczema.

<30> The use of AGR2 and/or AGR3 as an index of a condition of skin dryness in a subject.

<31> The use according to <30>, wherein AGR2 and AGR3 are preferably used in combination.

<32> The use according to <30> or <31>, wherein the expression levels of AGR2 and/or AGR3 are preferably used as the index, and the levels of AGR2 and/or AGR3 mRNA or the expression levels of the AGR2 protein and/or AGR3 protein are more preferably used as the index.

EXAMPLES

The present invention will now be described in more detail by way of examples thereof.

(Samples)

Skin tissue was collected by punch biopsy from the leg site of 7 people with dry skin symptoms and 6 healthy people among Caucasian healthy females living in USA (in their 20's to 40's) and used as a sample.

Example 1

Comparison of Expression Patterns of AGR2 and AGR3 in Skin Tissue

The skin tissue collected as a sample was embedded in OCT compound (Sakura Tissue Tek) and frozen. After this, a section with a thickness of 7 μm was made with a cryotome, and the tissue section was fixed with cold acetone. After this, non-specific binding was inhibited with Protein Block Serum-Free Ready to Use (Dako). Primary antigen: Anti-AGR2 (abcam) or Anti-AGR3 (abcam) was diluted in Can get signal solution (TOYOBO) and incubated for an hour. After this, secondary antigen: Alexa555 anti-Rabbit (Life Technologies) and Alexa555 anti-Mouse (Life Technologies) were diluted in Can get signal solution and incubated for 30 minutes for visualization.

The results are shown in FIG. 1. AGR2 and AGR3 were localized and expressed on the upper part of living epidermal cell region of skin. Although the localized regions of AGR2 and AGR3 were not different between healthy people and people with dry skin, the expression strength was obviously weak in the people with dry skin.

Example 2

Comparison of Expression Levels of AGR2 and AGR3 in Skin Tissue

The skin tissue collected as a sample (7 people with dry skin and 6 healthy people) was soaked in Dispase solution, and separated into the epidermis and derma. The obtained epidermal tissue was soaked in RNA later (QIAGEN) and stored at −80° C. until used. After this, total RNA was extracted using RNeasy (Registered Trademark) Mini Kit (QIAGEN). The concentration of total RNA was measured and a reverse transcription reaction was carried out using a constant amount of total RNA. High capacity RNA-to-cDNA kit (Applied Biosystems) was used for the reverse transcription reaction. The expression of AGR2 and AGR3 mRNA was quantitatively determined from the obtained cDNA by Real-Time PCR. Taqman (Registered Trademark) Probes (AGR2: Hs00180702_m1, AGR3: Hs00411286_m1, Applied Biosystems) were used for quantitative determination, and PRISM 7500 (Applied Biosystems) was used for detection and quantitative determination. PCR was carried out in a 20 μL reaction system and the amplification conditions were a denaturation reaction at 95° C. for 15 seconds, annealing at 60° C. for a minute and an elongation reaction. The expression level of each gene was normalized with the expression level of RPLP0 (Hs99999902_m1, Applied Biosystems) and shown as a relative value in the case where each mean expression level of AGR2 and AGR3 in healthy people was considered as 1.

The results are shown in FIG. 2. The expression levels of AGR2 and AGR3 in skin of people with dry skin significantly decreased compared to those of healthy people.

Example 3

Correlation Between Expression Levels of AGR2 and AGR3 and Degrees of Skin Dryness The skin dryness score and horny layer conductance in subjects (13 people) were examined. As the skin dryness score, the dry condition of a target site was visually evaluated by two examiners using 5 levels (0: no dryness, 1: slight flaking is observed, 2: moderate flaking and/or scaling are observed, 3: marked scaling and/or slight fissuring are observed, and 4: severe scaling and/or fissuring are observed), and the mean value was acquired. The horny layer conductance was measured by Skicon200EX (IBS Inc.). The skin tissue on the leg site was collected from each subject using punch biopsy. By the same procedure as in Example 2, the epidermal tissue was separated from the collected skin tissue, total RNA was extracted, the mRNA expression levels were quantitatively determined by RT-PCR, the measured value was normalized with the RPLP0 expression level, and each expression level of AGR2 and AGR3 was then measured. By Spearman's rank correlation coefficient test, each correlation efficient between skin dryness score and horny layer conductance was obtained about each of the expression levels of AGR2 and AGR3 measured from each subject. The results are shown in Table 1. The expression levels of AGR2 and AGR3 both were significantly correlated with both dryness score and horny layer conductance, which are indexes of a condition of skin dryness. Therefore, it was shown that the expression levels of AGR2 and/or AGR3 are an index to indicate a condition of skin dryness.

TABLE 1

|  | Dryness Score | Conductance |
| --- | --- | --- |
| AGR2 expression | −0.821 | 0.695 |
|  | ($p < 0.01$) | ($p < 0.05$) |
| AGR3 expression | −0.560 | 0.574 |
|  | ($p < 0.05$) | ($p < 0.05$) |

Example 4

Analysis of Promoting Action of Humectant on AGR2 Gene Expression Level

The normal human epidermal cells (NHEK) were cultured under conditions of 37° C. and 5% $CO_2$ using EpiLife (Registered Trademark) (purchased from Kurabo). The cells were seeded in a 12 well plate at $1 \times 10^5$ cells and cultured for 48 hours, and the medium was then exchanged with a serum-free medium. Further, vitamin $D_3$, which is a known agent for ameliorating dry skin, (99.5% ethanol solution, final concentration 1 nM or 10 nM) (Nutrients, 4(9):1213-8, 2012), eucalyptus extract (50% ethanol solution, final concentration 0.001%) (J Cosmet Dermatol, 12(1):3-11, 2013), macrocarpal, which is a major physiologically active substance of eucalyptus extract (50% ethanol solution, final concentration 10 nM) (Int J Cosmet Sci, 34(1):17-22, 2012), or 99.5% ethanol or 50% ethanol as a control was added to the medium. After 72 hour culture, total RNA was extracted from cells using RNeasy (Registered Trademark) Mini Kit (QIAGEN). The concentration of total RNA was measured and a reverse transcription reaction was carried out using a constant amount of total RNA. High capacity RNA-to-cDNA kit (Applied Biosystems) was used for the reverse transcription reaction. The expression of AGR2 mRNA was quantitatively determined from the obtained cDNA by Real-Time PCR. Taqman (Registered Trademark) Probe (AGR2: Hs00180702_m1, Applied Biosystems) was used for quantitative determination, and PRISM 7500 (Applied Biosystems) was used for detection and quantitative determination. PCR was carried out in a 20 μL reaction system and the amplification conditions were a denaturation reaction at 95° C. for 15 seconds, annealing at 60° C. for a minute and an elongation reaction. The mRNA expression level was normalized with the expression level of RPLP0 (Hs99999902_m1, Applied Biosystems) and shown as a relative value in the case where the mean expression level of AGR2 in a control (only 99.5% EtOH solvent) was considered as 1.

The results are shown in FIG. 3 and Table 2. In vitamin $D_3$, eucalyptus extract and macrocarpal, the AGR2 expression increased compared to that in the control.

TABLE 2

| Test substance | ARG2 expression level (Relative value) |
| --- | --- |
| Vitamin $D_3$ (1 nM) | 1.05 |
| Vitamin $D_3$ (10 nM) | 1.17 |
| *Eucalyptus* extract (0.001%) | 1.08 |
| Macrocarpal (10 nM) | 1.17 |

The invention claimed is:

1. A method of treating dry skin, the method comprising:
measuring the expression levels of AGR2 and/or AGR3 in skin cells collected from a test subject, wherein the skin cells comprise living subcorneal skin cells;
identifying the test subject as a subject suffering from dry skin when the measured expression levels of AGR2 and/or AGR3 is 50% or less than a reference value 2, wherein said reference value 2 is a mean value of the expression levels of AGR2 and/or AGR3 in living epidermal cells collected from a control group of subjects known to have non-dry skin; and
administering an agent to said identified subject suffering from dry skin, wherein said agent is selected from the group consisting of vitamin $D_3$, eucalyptus extract, and macrocarpal.

2. The method according to claim 1, wherein said subject suffering from dry skin has rough skin caused by skin dryness.

3. The method according to claim 2, wherein the rough skin caused by skin dryness is selected from the group consisting of, sensitive skin, xeroderma, senile xerosis, ichthyosis and dry eczema.

4. The method according to claim 1, wherein said subject suffering from dry skin has a measured expression level of AGR2 and/or AGR3 of 30% or less than said reference value 2.

5. The method according to claim 1, wherein said subject suffering from dry skin has a measured expression level of AGR2 and/or AGR3 of 25% or less than said reference value 2.

6. The method according to claim 1, wherein said agent is vitamin $D_3$.

7. The method according to claim 1, wherein said agent is eucalyptus extract.

8. The method according to claim 1, wherein said agent is macrocarpal.

\* \* \* \* \*